(12) United States Patent
Joo et al.

(10) Patent No.: US 9,433,593 B1
(45) Date of Patent: Sep. 6, 2016

(54) COMPOSITION FOR ANTI-INFLAMMATION CONTAINING 5-ADAMANTAN-1-YL-N-(2,4-DIHYDROXY-BENZYL)-2,4-DIMETHOXY-BENZAMIDE

(71) Applicant: Amorepacific Corporation, Seoul (KR)

(72) Inventors: Yung Hyup Joo, Gyeonggi-do (KR); Heung Soo Baek, Gyeonggi-do (KR); Jeong Hwan Kim, Gyeonggi-do (KR); Chang Geun Yi, Gyeonggi-do (KR); Hyung Jun Lim, Gyeonggi-do (KR); Hong-Ju Shin, Gyeonggi-do (KR); Yongjin Kim, Gyeonggi-do (KR); Jon Hwan Lee, Gyeonggi-do (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 15/085,628

(22) Filed: Mar. 30, 2016

(30) Foreign Application Priority Data

Mar. 31, 2015 (KR) .................... 10-2015-0045435

(51) Int. Cl.
| | | |
|---|---|---|
| *A61K 31/166* | (2006.01) | |
| *A61K 9/20* | (2006.01) | |
| *A61K 9/16* | (2006.01) | |
| *A61K 9/06* | (2006.01) | |
| *A23L 1/30* | (2006.01) | |
| *A61K 9/00* | (2006.01) | |

(52) U.S. Cl.
CPC .............. *A61K 31/166* (2013.01); *A23L 1/30* (2013.01); *A61K 9/0014* (2013.01); *A61K 9/0056* (2013.01); *A61K 9/06* (2013.01); *A61K 9/16* (2013.01); *A61K 9/20* (2013.01); *A23V 2002/00* (2013.01)

(58) Field of Classification Search
None
See application file for complete search history.

(56) References Cited

U.S. PATENT DOCUMENTS

2014/0234241 A1    8/2014    Joo et al.

FOREIGN PATENT DOCUMENTS

KR    10-2013-0015954 A    2/2013

*Primary Examiner* — Yevegeny Valenrod
(74) *Attorney, Agent, or Firm* — Blank Rome LLP

(57) ABSTRACT

5-Adamantan-1-yl-N-(2,4-dihydroxybenzyl)-2,4-dimethoxybenzamide disclosed in the present disclosure lacks toxicity and can exhibit superior anti-inflammatory effect. It exhibits superior anti-inflammatory effect, for example, by inhibiting the production of one or more of NO and PGE2, by inhibiting the activity of one or more of the transcription factors NF-κB and AP-1 or by inhibiting proinflammatory cytokines such as IL-1β.

9 Claims, 7 Drawing Sheets

COMPOSITION FOR ANTI-INFLAMMATION CONTAINING 5-ADAMANTAN-1-YL-N-(2,4-DIHYDROXY-BENZYL)-2,4-DIMETHOXY-BENZAMIDE

CROSS-REFERENCE TO RELATED APPLICATION

This application claims the priority of Korean Patent Application No. 10-2015-0045435, filed on Mar. 31, 2015, and all the benefits accruing therefrom under 35 U.S.C. §119, the contents of which in its entirety are herein incorporated by reference.

BACKGROUND

1. Field

The present disclosure relates to 5-adamantan-1-yl-N-(2,4-dihydroxybenzyl)-2,4-dimethoxybenzamide and a composition containing the same for use in anti-inflammation.

2. Description of the Related Art

Inflammation is a complicated biological process involving activation of various immune cells such as monocytes and macrophages. Dysregulation of inflammatory immune response leads to various pathological conditions including cancer and metabolic syndrome. Macrophages are important cells involved in inflammation because they produce various inflammatory mediators such as cytokines/chemokines, nitric oxide (NO) and prostaglandins (PGs). iNOS (inducible NO synthase) is an enzyme which synthesizes NO from L-arginine using NADPH and oxygen molecules. COX-2 (cyclooxygenase-2) converts arachidonic acid to prostaglandin such as PGE2. Downregulation of inflammatory mediators in macrophages provides a theoretical basis for development of therapeutic materials useful for various inflammatory diseases.

Various transfer factors and cellular signal transduction pathways are involved in the expression of proinflammatory genes in macrophages. NF-κB is activated via activation of the IκB-kinase (IKK) complex under stimulation by lipopolysaccharides (LPS) or cytokines. The IKK complex consists of two kinase subunits, IKKα and IKKβ, and a regulatory subunit IKKγ (NEMO). The IKK complex is ubiquitinated via phosphorylation of IκBα on Ser32 and Ser36, leading to proteosomal degradation. Free NF-κB is separated from cytoplasmic IκBα and migrates into the nucleus, thereby activating the transcription of target genes such as proinflammatory genes in the nucleus.

SUMMARY

In an aspect, the present disclosure is directed to providing a composition which lacks toxicity and has superior anti-inflammatory activity.

In an aspect, the present disclosure provides a composition for anti-inflammation containing 5-adamantan-1-yl-N-(2,4-dihydroxybenzyl)-2,4-dimethoxybenzamide, an isomer thereof, a pharmaceutically acceptable salt thereof, a prodrug thereof, a hydrate thereof or solvate thereof as an active ingredient.

In an exemplary embodiment, the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may inhibit the production of one or more of NO and PGE2.

In another exemplary embodiment, the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may inhibit the expression of one or more of iNOS and COX-2.

In another exemplary embodiment, the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may inhibit the activity of one or more of the transcription factors NF-κB and AP-1.

In another exemplary embodiment, the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may inhibit the expression of proinflammatory cytokines.

In another exemplary embodiment, the proinflammatory cytokine may be IL-1β.

In another exemplary embodiment, the composition of the present disclosure may be a cosmetic, food or pharmaceutical composition.

In an aspect of the present disclosure, the composition containing 5-adamantan-1-yl-N-(2,4-dihydroxybenzyl)-2,4-dimethoxybenzamide, an isomer thereof, a pharmaceutically acceptable salt thereof, a prodrug thereof, a hydrate thereof or a solvate thereof as an active ingredient may lack toxicity and exhibit superior anti-inflammatory effect.

The composition for anti-inflammation according to an aspect of the present disclosure is effective in inhibiting the production of one or more of NO and PGE2.

The composition for anti-inflammation according to an aspect of the present disclosure is effective in inhibiting the expression of one or more of iNOS and COX-2.

The composition for anti-inflammation according to an aspect of the present disclosure is effective in inhibiting the activity of one or more of the transcription factors NF-κB and AP-1.

The composition for anti-inflammation according to an aspect of the present disclosure exhibits superior anti-inflammatory effect by inhibiting the expression of the proinflammatory cytokine IL-1β.

DETAILED DESCRIPTION

Figure 1:
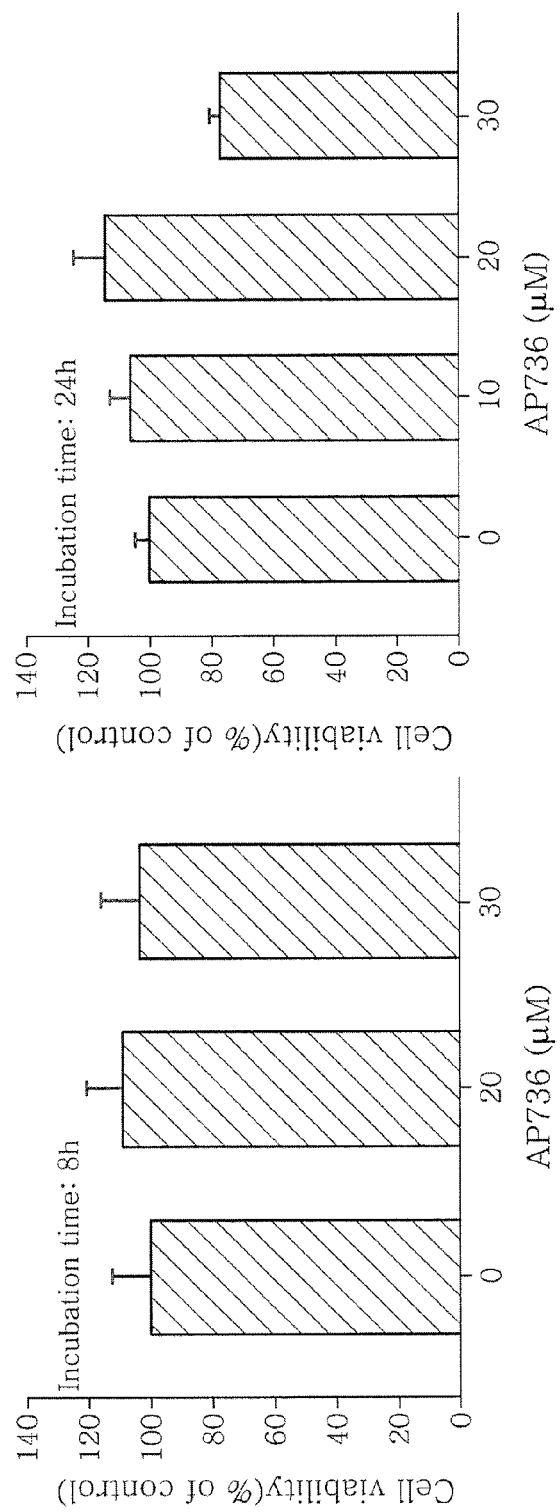
FIG. 1 shows the cell viability of RAW 264.7 cells treated with 5-adamantan-1-yl-N-(2,4-dihydroxybenzyl)-2,4-dimethoxybenzamide (denoted as 'AP736' in FIG. 1).

In an aspect of the present disclosure, the present disclosure relates to a composition for anti-inflammation containing 5-adamantan-1-yl-N-(2,4-dihydroxybenzyl)-2,4-dimethoxybenzamide of Chemical Formula 1, an isomer thereof, a pharmaceutically acceptable salt thereof, a prodrug thereof, a hydrate thereof or a solvate thereof as an active ingredient:

[Chemical Formula 1]

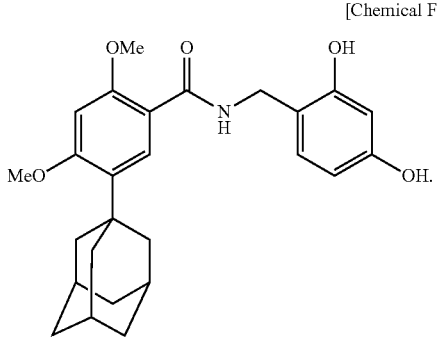

In an aspect of the present disclosure, the present disclosure provides a method for suppressing inflammation in a subject, which includes administering an effective amount of 5-adamantan-1-yl-N-(2,4-dihydroxybenzyl)-2,4-dimethoxybenzamide, an isomer thereof, a pharmaceutically acceptable salt thereof, a prodrug thereof, a hydrate thereof or a solvate thereof to a subject in need thereof.

In an aspect of the present disclosure, the present disclosure provides a use of 5-adamantan-1-yl-N-(2,4-dihydroxybenzyl)-2,4-dimethoxybenzamide, an isomer thereof, a pharmaceutically acceptable salt thereof, a prodrug thereof, a hydrate thereof or a solvate thereof in preparing a composition for anti-inflammation.

In an aspect of the present disclosure, the present disclosure provides a 5-adamantan-1-yl-N-(2,4-dihydroxybenzyl)-2,4-dimethoxybenzamide, an isomer thereof, a pharmaceutically acceptable salt thereof, a prodrug thereof, a hydrate thereof or a solvate thereof for anti-inflammation.

In an exemplary embodiment, the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may inhibit the production of one or more of NO and PGE2.

In another exemplary embodiment, the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may inhibit the expression of one or more of iNOS and COX-2.

In another exemplary embodiment, the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may inhibit the activity of one or more of the transcription factors NF-κB and AP-1.

In another exemplary embodiment, the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may inhibit proinflammatory cytokines.

In another exemplary embodiment, the proinflammatory cytokine may be IL-1β.

In another aspect of the present disclosure, the composition for anti-inflammation may be a cosmetic, food or pharmaceutical composition.

In an exemplary embodiment of the present disclosure, the present disclosure provides a composition containing 5-adamantan-1-yl-N-(2,4-dihydroxybenzyl)-2,4-dimethoxybenzamide, an isomer thereof, a pharmaceutically acceptable salt thereof, a prodrug thereof, a hydrate thereof or a solvate thereof as an active ingredient.

In an aspect of the present disclosure, 5-adamantan-1-yl-N-(2,4-dihydroxybenzyl)-2,4-dimethoxybenzamide may be prepared as follows.

In an aspect of the present disclosure, the present disclosure provides a method for preparing an adamantane-substituted benzamide compound, which includes:

i) a step of synthesizing adamantanylhydroxybenzoic acid by reacting hydroxybenzoic acid and an adamantane compound in the presence of an acid catalyst;

ii) a step of synthesizing an adamantanylalkoxybenzoic acid by reacting the adamantanylhydroxybenzoic acid with an alkyl sulfate; and iii) a step of synthesizing an adamantane-substituted benzamide compound by reacting the adamantanylalkoxybenzoic acid with a hydroxy-substituted alkylphenylamine.

The method for preparing an adamantane-substituted benzamide compound according to an aspect of the present disclosure may be schematized by Scheme 1:

[Scheme 1]

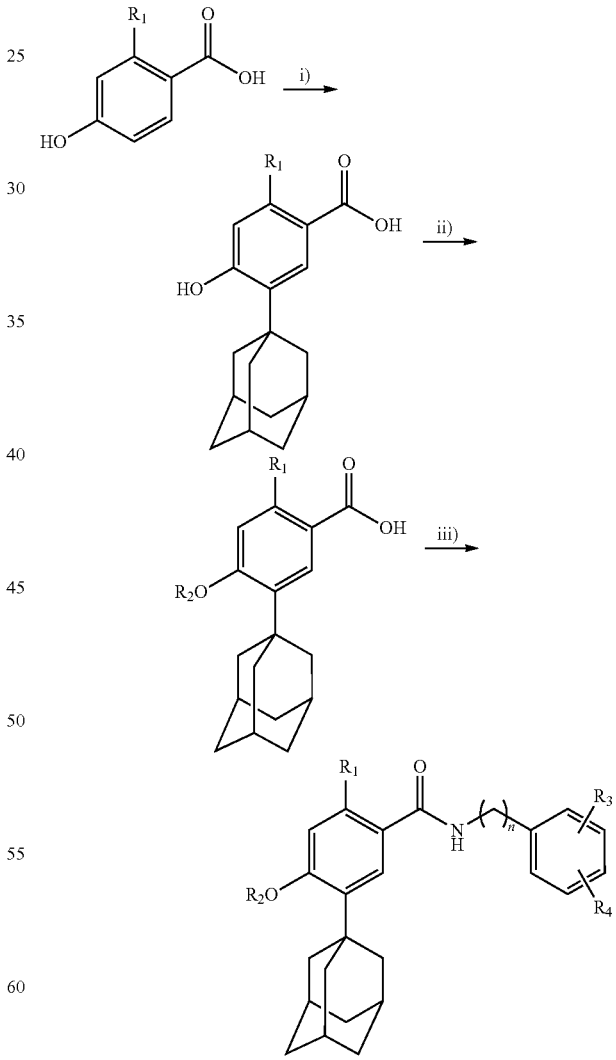

In Scheme 1, each of $R_1$, $R_3$ and $R_4$ is independently selected from a group consisting of hydrogen, hydroxy, $C_1$-$C_6$ alkoxy, $C_3$-$C_6$ cycloalkoxy, aryloxy and $C_1$-$C_6$ haloalkoxy, $R_2$ is selected from a group consisting of hydrogen, $C_1$-$C_6$ alkyl, $C_3$-$C_6$ cycloalkyl, aryl and $C_1$-$C_5$ haloalkyl, and n is an integer selected from 1 to 5.

A method for preparing an adamantane-substituted benzamide compound according to another aspect of the present disclosure may include:

i) a step of synthesizing adamantanyldihydroxybenzoic acid by reacting dihydroxybenzoic acid with an adamantane compound in the presence of an acid catalyst;

ii) a step of synthesizing adamantanylhydroxyalkoxybenzoic acid or an adamantanyldialkoxybenzoic acid by reacting adamantanyldihydroxybenzoic acid with a dialkyl sulfate in the presence of a hydroxide salt; and iii) a step of synthesizing an adamantane-substituted benzamide compound by reacting adamantanylhydroxyalkoxybenzoic acid or a adamantanyldialkoxybenzoic acid with hydroxy-substituted benzylamine or phenethylamine.

A method for preparing an adamantane-substituted benzamide compound according to another aspect of the present disclosure may include:

i) a step of synthesizing 5-adamantanyl-2,4-dihydroxybenzoic acid by reacting 2,4-dihydroxybenzoic acid with 1-adamantanol at room temperature in a dichloromethane solvent in the presence of acetic acid and sulfuric acid catalysts;

ii) a step of synthesizing 5-adamantanyl-2-hydroxy-4-methoxybenzoic acid or 5-adamantanyl-2,4-dimethoxybenzoic acid by reacting 5-adamantanyl-2,4-dihydroxybenzoic acid with dimethyl sulfate in the presence of sodium hydroxide or potassium hydroxide; and iii) a step of synthesizing an adamantane-substituted benzamide compound by reacting 5-adamantanyl-2-hydroxy-4-methoxybenzoic acid or 5-adamantanyl-2,4-dimethoxybenzoic acid with hydroxy-substituted benzylamine or phenethylamine in the presence of N-hydroxysuccinimide (HOSu) and N,N'-dicyclohexylcarbodiimide (DCC).

5-Adamantan-1-yl-N-(2,4-dihydroxybenzyl)-2,4-dimethoxybenzamide prepared by the process described above, an isomer thereof, a pharmaceutically acceptable salt thereof, a prodrug thereof, a hydrate thereof or a solvate thereof has anti-inflammatory effect.

In an aspect, the present disclosure provides a composition containing the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof, which has anti-inflammatory effect, as an active ingredient.

The composition according to an aspect of the present disclosure may contain 0.01-20 wt % of the compound, the isomer thereof, the pharmaceutically acceptable salt thereof, the prodrug thereof, the hydrate thereof or the solvate thereof based on the total weight of the composition.

In an aspect, the amount of the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may be 0.01 wt % or more, 0.02 wt % or more, 0.03 wt % or more, 0.04 wt % or more, 0.05 wt % or more, 0.1 wt % or more, 0.2 wt % or more, 0.3 wt % or more, 0.4 wt % or more, 0.5 wt % or more, 0.6 wt % or more, 0.7 wt % or more, 0.8 wt % or more, 0.9 wt % or more, 1.0 wt % or more, 2.0 wt % or more, 3.0 wt % or more, 4.0 wt % or more, 4.1 wt % or more, 4.2 wt % or more, 4.3 wt % or more, 4.4 wt % or more, 4.5 wt % or more, 4.6 wt % or more, 4.7 wt % or more, 4.8 wt % or more, 4.9 wt % or more or 5.0 wt % or more based on the total weight of the composition.

In an aspect, the amount of the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof may be 20 wt % or less, 19.5 wt % or less, 19 wt % or less, 18 wt % or less, 17 wt % or less, 16 wt % or less, 15 wt % or less, 14 wt % or less, 13 wt % or less, 12 wt % or less, 11 wt % or less, 10 wt % or less, 9 wt % or less, 8 wt % or less, 7 wt % or less, 6 wt % or less, 5.9 wt % or less, 5.8 wt % or less, 5.7 wt % or less, 5.6 wt % or less, 5.5 wt % or less, 5.4 wt % or less, 5.3 wt % or less, 5.2 wt % or less or 5.1 wt % or less based on the total weight of the composition.

When the amount of the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof is within the above-described range, the effect desired by the present disclosure may be achieved adequately and both the stability and safety of the composition may be satisfactory. The above-described range may also be adequate in terms of cost effectiveness. Specifically, when the amount of the 5-adamantan-1-yl-N-(2,4-dihydroxybenzyl)-2,4-dimethoxybenzamide, the isomer thereof, the pharmaceutically acceptable salt thereof, the prodrug thereof, the hydrate thereof or the solvate thereof is within the above-described range, anti-inflammatory effect may be achieved effectively without toxicity.

In an exemplary embodiment, the composition may be a cosmetic, food or pharmaceutical composition.

The pharmaceutical composition according to the present disclosure may be prepared into various oral or parenteral formulations. The formulation is prepared by using a commonly used diluent or excipient such as a filler, an extender, a binder, a humectant, a disintegrant, a surfactant, etc. Solid formulations for oral administration include a tablet, a pill, a powder, a granule, a soft or hard capsule, etc. These solid formulations are prepared by mixing one or more of the above compound with at least one excipient, e.g., starch, calcium carbonate, sucrose, lactose, gelatin, etc. In addition to the simple excipient, a lubricant such as magnesium stearate, talc, etc. is also used. Liquid formulations for oral administration include a suspension, a liquid formulation for internal use, an emulsion, a syrup, etc. In addition to a commonly used simple diluent such as water and liquid paraffin, various excipients such as a humectant, a sweetener, an aromatic, a preservative, etc. may be contained in the formulation. Formulations for parenteral administration include a sterilized aqueous solution, a nonaqueous solution, a suspension, an emulsion, a freeze-dried formulation and a suppository. In the nonaqueous solution or suspension, propylene glycol, polyethylene glycol, a vegetable oil such as olive oil, an injectable ester such as ethyl oleate, etc. may be used as a solvent. As a base of the suppository, witepsol, macrogol, Tween 61, cocoa butter, laurin butter, glycerogelatin, etc. may be used.

The composition of the present disclosure may be pharmaceutically administered in the form of a pharmaceutically acceptable salt either alone or in appropriate combination with another pharmaceutically active compound. The salt is not particularly limited as long as it is pharmaceutically acceptable. For example, hydrochloride, sulfate, nitrate, phosphate, hydrofluoride, hydrobromide, formate, acetate, tartrate, lactate, citrate, fumarate, maleate, succinate, methanesulfonate, benzenesulfonate, toluenesulfonate, naphthalenesulfonate, etc. may be used.

The composition of the present disclosure may be administered parenterally or orally depending on purposes. A daily dosage of 0.01-500 mg, specifically 0.1-100 mg, per kg body weight may be administered at once or may be divided into a number of smaller doses. The administration dosage for a particular patient may vary depending on the body weight, age, sex, physical condition and diet of the patient, administration time, administration method, rate of excretion, severity of a disease, etc.

The pharmaceutical composition according to the present disclosure may be prepared into any pharmaceutically suitable formulation including an oral formulation such as a powder, a granule, a tablet, a soft or hard capsule, a suspension, an emulsion, a syrup, an aerosol, etc., a formulation for external application such as an ointment, a cream, etc., a suppository, an injection, a sterilized solution for injection, etc. according to common methods.

The composition according to the present disclosure may be administered to a mammal such as rat, mouse, cattle, human, etc. via various parenteral and oral routes. Any mode of administration may be expected. For example, it may be administered orally, rectally, intravenously, intramuscularly, subcutaneously, intrauterinarily or intracerebroventricularly.

In an aspect of the present disclosure, the food composition may be a health functional food composition.

The formulation of the food composition according to the present disclosure is not particularly limited. For example, it may be formulated as a tablet, a granule, a powder, a liquid formulation such as a drink, a caramel, a gel, a bar, etc. Each formulation of the food composition may contain, in addition to the active ingredient, an ingredient commonly used in the art which may be selected by those skilled in the art considering the particular formulation or purpose of use. In this case, a synergic effect may be achieved.

Determination of the administration dosage of the active ingredient in the food composition according to the present disclosure is within the level of those skilled in the art. A daily administration dosage may be, for example, 0.1-5000 mg/kg/day, more specifically 1-500 mg/kg/day. However, the administration dosage may vary depending on various factors such as the age and health condition of a subject, presence of a complication, etc., without being limited thereto.

The food composition according to the present disclosure may be various foods, e.g., chewing gum, caramel, candy, frozen dessert, confectionery, etc., drinks such as soft drink, mineral water, alcoholic beverage, etc. or health functional foods including vitamins, minerals, etc.

Furthermore, the food composition according to an aspect of the present disclosure may further contain various nutrients, vitamins, minerals (electrolytes), flavors such as synthetic and natural flavors, colorants, extenders (cheese, chocolate, etc.), pectic acid and salts thereof, alginic acid and salts thereof, organic acids, protective colloidal thickeners, pH control agents, stabilizers, antiseptics, glycerin, alcohols, carbonating agents used in carbonated drinks, etc. In addition, the functional food composition of the present disclosure may contain a pulp for preparing natural fruit juice, fruit juice drink or vegetable drink. These ingredients may be used independently or in combination. The addition amount of these additives is of no great importance. Usually, they are contained in an amount of about 0-20 parts by weight per 100 parts by weight of the composition of the present disclosure.

The formulation of the cosmetic composition is not particularly limited and may be determined adequately depending on purposes. For example, it may be prepared into one or more formulation consisting of a skin lotion, a skin softener, a skin toner, an astringent, a lotion, a milk lotion, a moisturizing lotion, a nourishing lotion, a massage cream, a nourishing cream, a moisturizing cream, a hand cream, a foundation, an essence, a nourishing essence, a pack, a soap, a cleansing foam, a cleansing lotion, a cleansing cream, a body lotion and a body cleanser, although not being limited thereto.

When the formulation of the present disclosure is a paste, a cream or a gel, animal fiber, plant fiber, wax, paraffin, starch, tragacanth, a cellulose derivative, polyethylene glycol, silicone, bentonite, silica, talc, zinc oxide, etc. may be used as a carrier component.

When the formulation of the present disclosure is a powder or a spray, lactose, talc, silica, aluminum hydroxide, calcium silicate or polyamide powder may be used as a carrier component. In particular, the spray may additionally contain a propellant such as a chlorofluorohydrocarbon, propane/butane or dimethyl ether.

When the formulation of the present disclosure is a solution or an emulsion, a solvent, a solubilizing agent or an emulsifier may be used as a carrier component. For example, water, ethanol, isopropanol, ethyl carbonate, ethyl acetate, benzyl alcohol, benzyl benzoate, propylene glycol, 1,3-butylene glycol, glycerol fatty ester, polyethylene glycol or sorbitan fatty acid ester may be used.

When the formulation of the present disclosure is a suspension, a liquid diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth, etc. may be used as a carrier component.

When the formulation of the present disclosure is a surfactant-containing cleanser, an aliphatic alcohol sulfate, an aliphatic alcohol ether sulfate, sulfosuccinic monoester, isethionate, an imidazolinium derivative, methyl taurate, sarcosinate, a fatty acid amide ether sulfate, an alkyl amidobetaine, an aliphatic alcohol, a fatty acid glyceride, a fatty acid diethanolamide, a vegetable oil, a lanolin derivative or an ethoxylated glycerol fatty acid ester, etc. may be used as a carrier component.

Although the content of the active ingredient is not particularly limited, it may be 0.01-20 wt % based on the total weight of the composition. When the content of the active ingredient is within the above range, superior effect may be achieved without any side effect.

The cosmetic composition may further contain a functional additive and an ingredient commonly contained in a cosmetic composition. The functional additive may be selected from a group consisting of a water-soluble vitamin, an oil-soluble vitamin, a polypeptide, a polysaccharide, a sphingolipid and a seaweed extract.

If necessary, the cosmetic composition of the present disclosure may further contain an ingredient commonly contained in a cosmetic composition together with the functional additive. The additionally contained ingredient may be an oil, a fat, a humectant, an emollient, a surfactant, an organic or inorganic pigment, an organic powder, a UV absorbent, an antiseptic, a sterilizer, an antioxidant, a plant extract, a pH control agent, an alcohol, a colorant, a fragrance, a blood circulation promoter, a cooling agent, an antiperspirant, purified water, etc.

EXAMPLES

Hereinafter, the present disclosure will be described in detail through an example and test examples. However, the following example and test examples are for illustrative purposes only and it will be apparent to those of ordinary skill in the art that the scope of the present disclosure is not limited by them.

Example

Preparation of 5-adamantan-1-yl-N-(2,4-dihydroxybenzyl)-2,4-dimethoxybenzamide 5-Adamantan-1-yl-2,4-dimethoxybenzoic acid (0.634 g), N-hydroxysuccinimide (0.24 g) and N,N'-dicyclohexylcarbodiimide (0.43 g) were dissolved in dioxane (10 mL) and stirred for 12 hours. After filtering the produced solid, the filtrate was added dropwise to a mixture solution of 2,4-dihydroxybenzylamine bromate (0.54 g), sodium bicarbonate (0.18 g) and water (2 mL) and the mixture was stirred at 50° C. for 2 hours. After the reaction was completed, the solution was cooled to room temperature, neutralized with a 10% HCl solution and then washed with ethyl acetate (50 mL). After drying the organic layer with anhydrous magnesium sulfate, followed by drying, filtration and concentration under reduced pressure, 0.14 g of the target substance was obtained as a white solid by separating by column chromatography.

A result of analyzing the white solid by NMR is as follows. The white solid was identified as 5-adamantan-1-yl-N-(2,4-dihydroxybenzyl)-2,4-dimethoxybenzamide.

$^1$H NMR (300 MHz, DMSO-d6) δ 9.67 (s, 1H), 9.13 (s, 1H), 8.51 (m, 1H), 7.78 (m, 1H), 6.92 (d, 1H, J=8.1 Hz), 6.66 (s, 1H), 6.27 (s, 1H), 6.16 (d, 1H, J=8.1 Hz), 4.30 (d, 2H, J=5.4 Hz), 3.93 (s, 3H), 3.88 (s, 3H), 1.98 (s, 9H), 1.71 (s, 6H).

Cell Culturing

RAW 264.7 cells (murine macrophage cell line) (ATCC, Rockville, Md., USA) and HEK 293 cells were cultured in RPMI 1640 medium supplemented with FBS (10% heat-inactivated fetal bovine serum; Gibco, Grand Island, N.Y., USA), glutamine and antibiotics (penicillin and streptomycin) at 37° C. under 5% $CO_2$.

In all experiments, the cells were detached with a cell scraper. When the cells were cultured to a density of $2 \times 10^6$ cells/mL, the ratio of dead cells was 1% or lower (determined by the trypan blue dye exclusion method)

Test Example 1

Cytotoxicity of 5-adamantan-1-yl-N-(2,4-dihydroxybenzyl)-2,4-dimethoxybenzamide In order to determine an optimal concentration for testing the anti-inflammatory effect of 5-adamantan-1-yl-N-(2,4-dihydroxybenzyl)-2,4-dimethoxybenzamide, cytotoxicity of the 5-adamantan-1-yl-N-(2,4-dihydroxybenzyl)-2,4-dimethoxybenzamide was investigated at different concentrations.

During subculturing, RAW 264.7 cells were plated on a well plate to a concentration of $1 \times 10^6$ cells/well. After culturing for 18 hours, the cells were treated with 5-adamantan-1-yl-N-(2,4-dihydroxybenzyl)-2,4-dimethoxybenzamide (denoted as 'AP736' in FIG. 1) at concentrations of 0-30 μM. Then, the cells were cultured in an incubator for 8 hours or 24 hours. Cytotoxicity was evaluated by the commonly used MTT method. 3 hours before the last culturing, 10 μL of an MTT (3-[4,5-dimethylthiazol-2-yl]-2,5-diphenyltetrazolium bromide) solution (10 mg/mL in phosphate-buffered saline, pH 7.4) was added to each well. After terminating reaction by adding 15% SDS (sodium dodecyl sulfate) to each well, the formed formazan crystals were dissolved. Then, absorbance was measured at 570 nm on a microplate reader.

The result is shown in FIG. 1. At 10 and 20 μM, 5-adamantan-1-yl-N-(2,4-dihydroxybenzyl)-2,4-dimethoxybenzamide did not show toxicity (cell viability 100%) in the RAW 264.7 cells when treated for 8 hours and 24 hours. The cell viability was close to 80% when the cells were cultured for 24 hours at the concentration of 30 μM.

Test Example 2

Effect of 5-adamantan-1-yl-N-(2,4-dihydroxybenzyl)-2,4-dimethoxybenzamide on NO and PGE2 Production RAW 264.7 cells ($1 \times 10^6$ cells/well) that had been preincubated for 18 hours were treated with 5-adamantan-1-yl-N-(2,4-dihydroxybenzyl)-2,4-dimethoxybenzamide (hereinafter, 'AP736') at concentrations of 0-30 μM for 30 minutes and then incubated for 6 hours or 24 hours with LPS (1 μg/mL). The supernatant was recovered after the incubation. The cells incubated for 6 hours were subjected to PGE2 analysis and those incubated for 24 hours were subjected to NO analysis. The NO concentration in the culture medium was measured by the Griess test (Promega, Madison, Wis., USA). And, the concentration of PGE2 released to the culture medium was measured using an EIA kit (Amersham, Little Chalfont, Buckinghamshire, UK).

Figure 2:
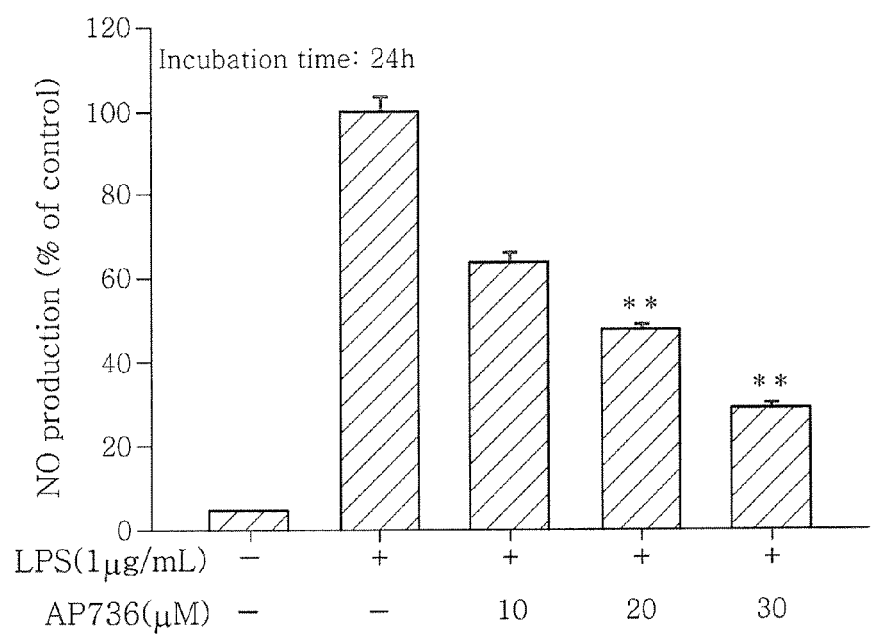
FIG. 2 and FIG. 3 show the production of NO and PGE2 in RAW 264.7 cells treated with 5-adamantan-1-yl-N-(2,4-dihydroxybenzyl)-2,4-dimethoxybenzamide.
Figure 3:
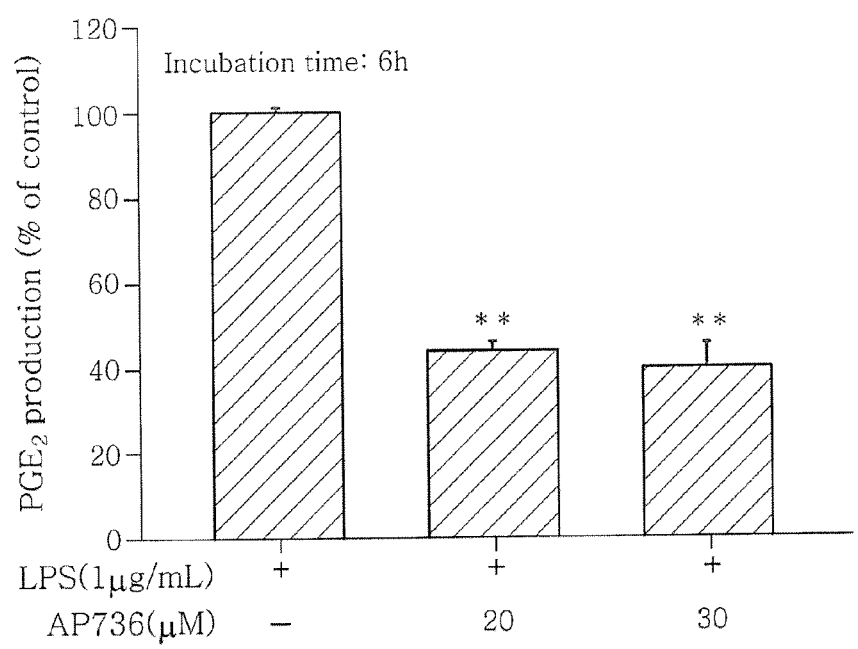

The result is shown in FIG. 2 and FIG. 3. The positive control group treated only with LPS (1 μg/mL) showed the highest NO production, whereas the groups treated with 5-adamantan-1-yl-N-(2,4-dihydroxybenzyl)-2,4-dimethoxybenzamide and LPS showed statistically significant decrease in NO production with increasing concentration of 5-adamantan-1-yl-N-(2,4-dihydroxybenzyl)-2,4-dimethoxybenzamide.

The PGE2 concentration measurement result also showed a similar pattern. The concentration of PGE2 decreased as compared to the group treated only with LPS with increasing concentration of 5-adamantan-1-yl-N-(2,4-dihydroxybenzyl)-2,4-dimethoxybenzamide.

Test Example 3

Effect of 5-adamantan-1-yl-N-(2,4-dihydroxybenzyl)-2,4-dimethoxybenzamide on Expression of iNOS, COX-2 and IL-1β

The expression level of iNOS, COX-2 and IL-1β which are known as inflammation-inducing factors was measured.

In order to investigate the effect of 5-adamantan-1-yl-N-(2,4-dihydroxybenzyl)-2,4-dimethoxybenzamide on inhibition of iNOS, COX-2 and IL-1β expression in RAW 264.7 cells, the cells were pretreated with 5-adamantan-1-yl-N-(2,4-dihydroxybenzyl)-2,4-dimethoxybenzamide at different concentrations and then RT-PCR was conducted after treating with LPS for 4 hours.

Figure 4A:
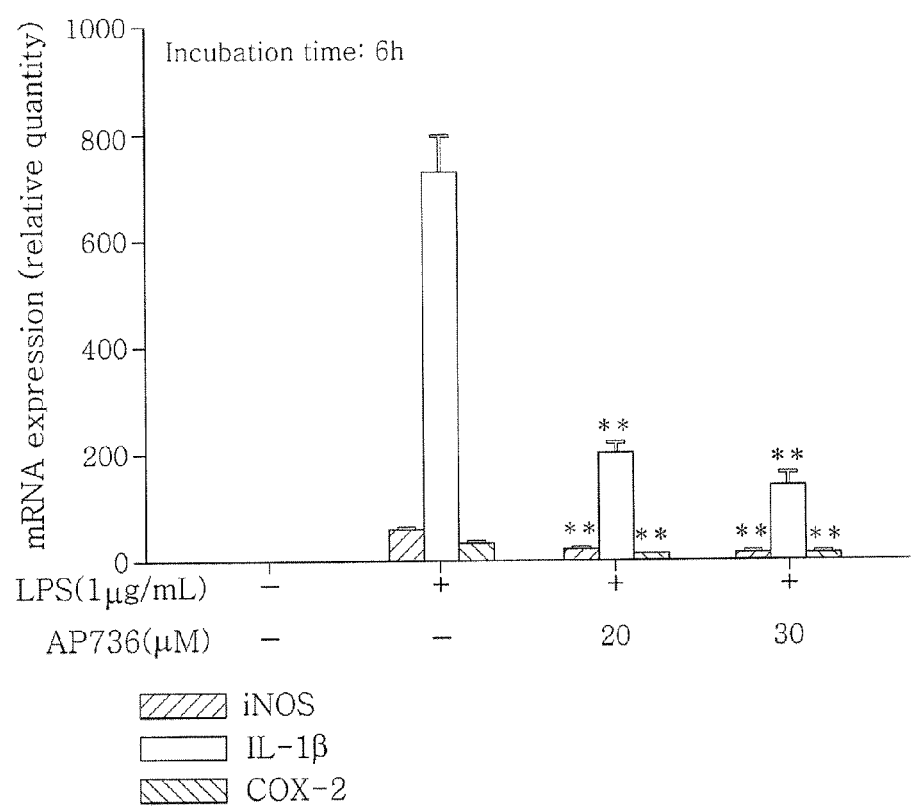
FIG. 4a-4b shows the expression of iNOS, COX-2 and IL-1β in RAW 264.7 cells treated with 5-adamantan-1-yl-N-(2,4-dihydroxybenzyl)-2,4-dimethoxybenzamide.
Figure 4B:
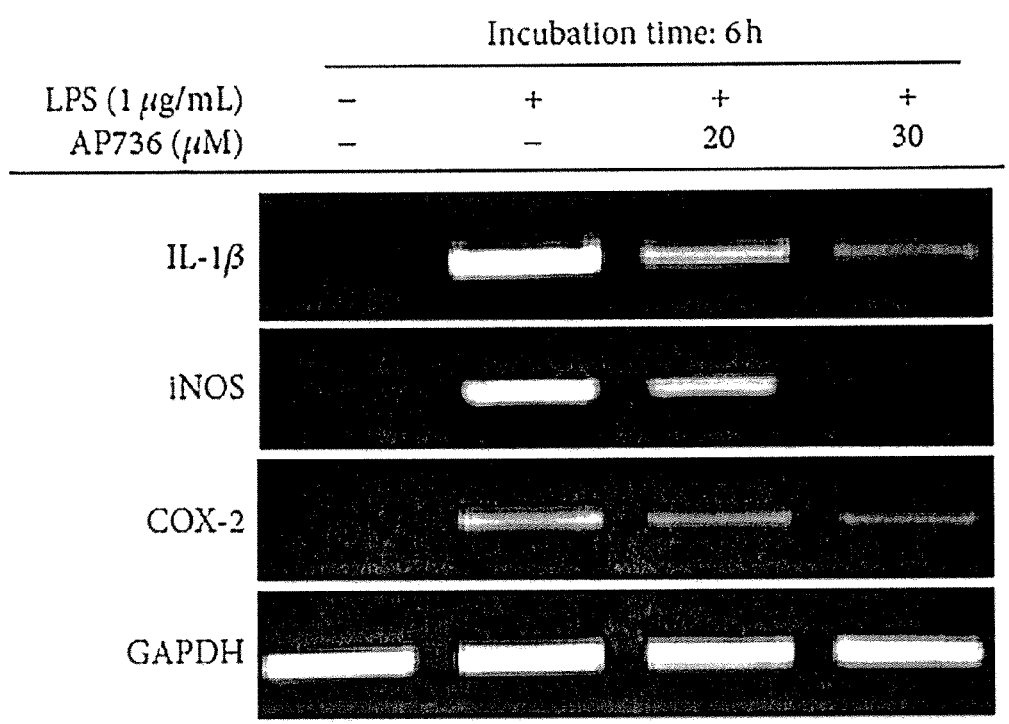

The result is shown in FIG. 4 (5-adamantan-1-yl-N-(2,4-dihydroxybenzyl)-2,4-dimethoxybenzamide is denoted as 'AP736' in FIG. 4). It was confirmed that the expression of the mRNAs and proteins of iNOS, COX-2 and IL-1β induced by LPS was distinctly inhibited by 5-adamantan-1-yl-N-(2,4-dihydroxybenzyl)-2,4-dimethoxybenzamide in a concentration-dependent manner. Accordingly, it was confirmed that the significant decrease the production of NO and PGE2 induced by LPS observed in Test Example 2 is due to the inhibited expression of iNOS and COX-2 mRNAs.

Also, it was confirmed that the expression of mRNAs of IL-1β, which is known to play an important role in inflammatory responses by activating T cells and macrophages and increasing other proinflammatory cytokines, is inhibited by 5-adamantan-1-yl-N-(2,4-dihydroxybenzyl)-2,4-dimethoxybenzamide in a concentration-dependent manner. Accordingly, it was confirmed that 5-adamantan-1-yl-N-(2,4-dihydroxybenzyl)-2,4-dimethoxybenzamide exhibits anti-inflammatory effect by inhibiting the expression of proinflammatory cytokines.

Test Example 4

Effect of 5-adamantan-1-yl-N-(2,4-dihydroxybenzyl)-2,4-dimethoxybenzamide on Activity of NF-κB and AP-1 Signaling Molecules Induced by LPS Experiment was conducted as follows to investigate whether 5-adamantan-1-yl-N-(2,4-dihydroxybenzyl)-2,4-dimethoxybenzamide regulates the transcriptional activity of inflammatory transcription factors.

The activity of transcription factors can be tested by the luciferase reporter gene assay. It is known that the activity of NF-κB and AP-1 is induced by the TLR adapter protein. NF-κB and AP-1 are known to produce the inflammatory factors NO and PGE2.

HEK 293 cells ($1 \times 10^6$ cells/well) were cotransfected with 1 μg of a plasmid containing NF-κB-Luc (luciferase) and AP-1-Luc constructs. The transfection was conducted on a 12-well plate by the PEI method. After 48 hours, the transformed cells were used for experiment. MyD88 or TRIF (1 μg/mL each), which are known as TLR adapter proteins, were cotransfected for 8 hours together with 5-adamantan-1-yl-N-(2,4-dihydroxybenzyl)-2,4-dimethoxybenzamide (5-adamantan-1-yl-N-(2,4-dihydroxybenzyl)-2,4-dimethoxybenzamide is denoted as 'AP736' in FIG. 5). The luciferase reporter gene assay was performed using the luciferase assay system (Promega, Madison, Wis.).

Figure 5A:
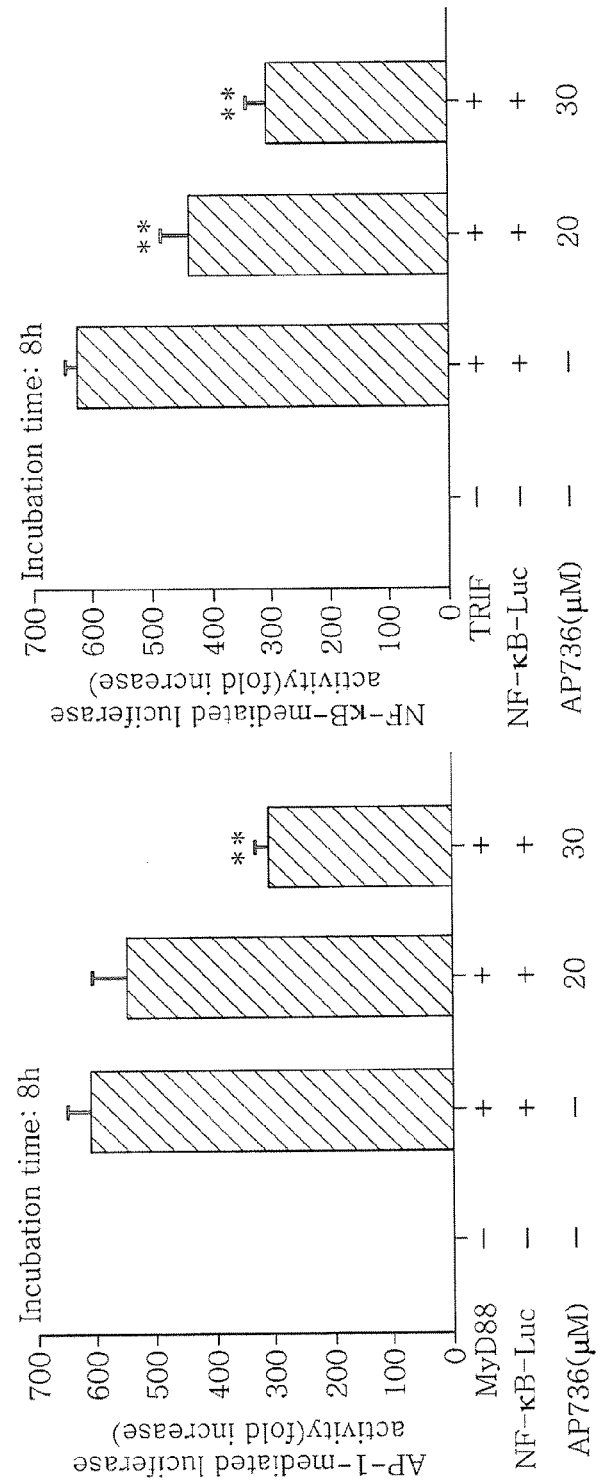
FIG. 5a-5b shows the effect of 5-adamantan-1-yl-N-(2,4-dihydroxybenzyl)-2,4-dimethoxybenzamide on the activity of the transcription factors NF-κB and AP-1 in HEK 293 cells.
Figure 5B:
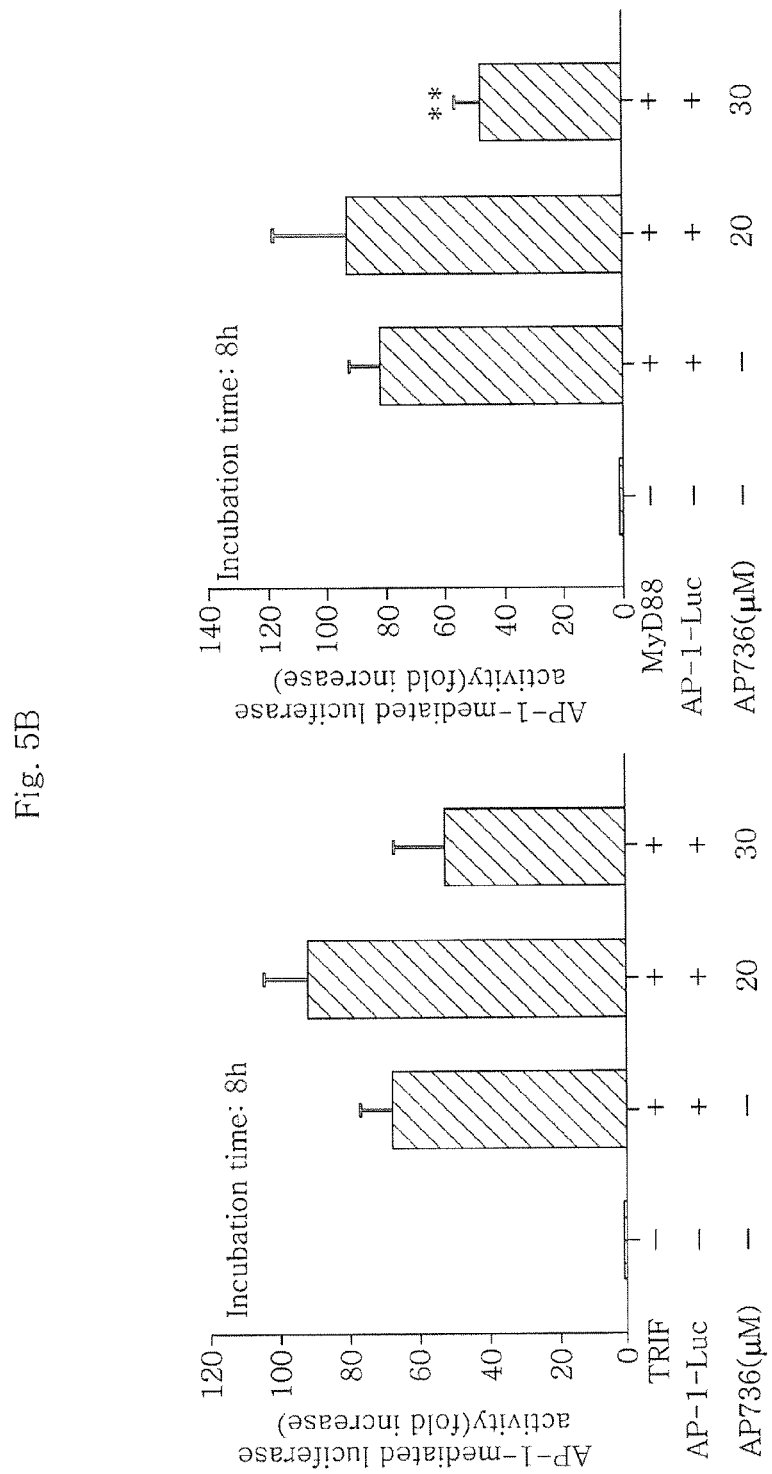

As seen from FIG. 5, treatment with 5-adamantan-1-yl-N-(2,4-dihydroxybenzyl)-2,4-dimethoxybenzamide resulted in decreased activity of NF-κB and AP-1. Accordingly, it was confirmed that 5-adamantan-1-yl-N-(2,4-dihydroxybenzyl)-2,4-dimethoxybenzamide exhibits significant anti-inflammatory effect by decreasing the activity of NF-κB and AP-1 which are transcription factors that produce the inflammatory factors NO and PGE2.

Hereinafter, the present disclosure will be described in detail through formulation examples. However, the following formulation examples are for illustrative purposes only and it will be apparent to those of ordinary skill in the art that the scope of the present disclosure is not limited by them.

| [Formulation Example 1] Health food | |
|---|---|
| 5-Adamantan-1-yl-N-(2,4-dihydroxybenzyl)-2,4-dimethoxybenzamide | 1 mg |
| Vitamin mixture | |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Mineral mixture | |
| Ferrous sulfate | 1.75 mg |
| Zinc oxide | 0.82 mg |
| Magnesium carbonate | 25.3 mg |
| Monopotassium phosphate | 15 mg |
| Dicalcium phosphate | 55 mg |
| Potassium citrate | 90 mg |
| Calcium carbonate | 100 mg |
| Magnesium chloride | 24.8 mg |

The compositional ratios of the vitamin and mineral mixtures described above, which are given as a specific example relatively suitable for a health food, may be varied as desired.

| [Formulation Example 2] Health drink | |
|---|---|
| 5-Adamantan-1-yl-N-(2,4-dihydroxybenzyl)-2,4-dimethoxybenzamide | 1 mg |
| Citric acid | 1000 mg |
| Oligosaccharide | 100 g |
| Taurine | 1 g |
| Purified water | balance |

According to a common health drink preparation method, the above ingredients are mixed and heated at 85° C. for about 1 hour under stirring. The resulting solution is filtered and sterilized.

Formulation Example 3

Tablet

After forming granules by mixing 0.1 mg of 5-adamantan-1-yl-N-(2,4-dihydroxybenzyl)-2,4-dimethoxybenzamide, 50 mg of soybean extract, 100 mg of glucose, 50 mg of red ginseng extract, 96 mg of starch and 4 mg of magnesium stearate and adding 40 mg of 30% ethanol, the granules are dried at 60° C. and prepared into tablets using a tableting machine.

Formulation Example 4

Granule

After forming granules by mixing 0.1 mg of 5-adamantan-1-yl-N-(2,4-dihydroxybenzyl)-2,4-dimethoxybenzamide, 50 mg of soybean extract, 100 mg of glucose and 600 mg of starch and adding 100 mg of 30% ethanol, the granules are dried at 60° C. and filled in a pouch.

Formulation Example 5

Lotion

A lotion is prepared by a common method with the composition described in Table 1.

TABLE 1

| Ingredients | Contents (wt %) |
|---|---|
| 5-Adamantan-1-yl-N-(2,4-dihydroxybenzyl)-2,4-dimethoxybenzamide | 0.1 |
| Glycerin | 3.0 |
| Butylene glycol | 2.0 |
| Propylene glycol | 2.0 |
| Carboxyvinyl polymer | 0.1 |
| PEG 12 nonyl phenyl ether | 0.2 |
| Polysorbate 80 | 0.4 |
| Ethanol | 10.0 |
| Triethanolamine | 0.1 |
| Antiseptic, pigment and fragrance | adequate |
| Purified water | balance |

Formulation Example 6

Nourishing Cream

A nourishing cream is prepared by a common method with the composition described in Table 2.

TABLE 2

| Ingredients | Contents (wt %) |
|---|---|
| 5-Adamantan-1-yl-N-(2,4-dihydroxybenzyl)-2,4- dimethoxybenzamide | 2.0 |
| Polysorbate 60 | 1.5 |
| Sorbitan sesquioleate | 0.5 |
| PEG 60 hydrogenated castor oil | 2.0 |
| Liquid paraffin | 10.0 |
| Squalane | 5.0 |
| Caprylic/capric triglyceride | 5.0 |
| Glycerin | 5.0 |
| Butylene glycol | 3.0 |
| Propylene glycol | 3.0 |
| Triethanolamine | 0.2 |
| Antiseptic, pigment and fragrance | adequate |
| Purified water | balance |

Formulation Example 7

Massage Cream

A massage cream is prepared by a common method with the composition described in Table 3.

TABLE 3

| Ingredients | Contents (wt %) |
|---|---|
| 5-Adamantan-1-yl-N-(2,4-dihydroxybenzyl)-2,4-dimethoxybenzamide | 1.0 |
| Beeswax | 10.0 |
| Polysorbate 60 | 1.5 |
| PEG 60 hydrogenated castor oil | 2.0 |
| Sorbitan sesquioleate | 0.8 |
| Liquid paraffin | 40.0 |
| Squalane | 5.0 |
| Caprylic/capric triglyceride | 4.0 |
| Glycerin | 5.0 |
| Butylene glycol | 3.0 |
| Propylene glycol | 3.0 |
| Triethanolamine | 0.2 |
| Antiseptic, pigment and fragrance | adequate |
| Purified water | balance |

Formulation Example 8

Pack

A pack is prepared by a common method with the composition described in Table 4.

TABLE 4

| Ingredients | Contents (wt %) |
|---|---|
| 5-Adaman an-1-yl-N-(2,4-dihydroxybenzyl)-2,4-dimethoxybenzamide | 0.2 |
| Polyvinyl alcohol | 13.0 |
| Sodium carboxymethyl cellulose | 0.2 |
| Glycerin | 5.0 |
| Allantoin | 0.1 |
| Ethanol | 6.0 |
| PEG 12 nonyl phenyl ether | 0.3 |
| Polysorbate 60 | 0.3 |
| Antiseptic, pigment and fragrance | adequate |
| Purified water | balance |

Formulation Example 9

Gel

A gel is prepared by a common method with the composition described in Table 5.

TABLE 5

| Ingredients | Contents (wt %) |
|---|---|
| 5-Adamantan-1-yl-N-(2,4-dihydroxybenzyl)-2,4-dimethoxybenzamide | 0.5 |
| Sodium ethylenediaminetetraacetate | 0.05 |
| Glycerin | 5.0 |
| Carboxyvinyl polymer | 0.3 |
| Ethanol | 5.0 |
| PEG 60 hydrogenated castor oil | 0.5 |
| Triethanolamine | 0.3 |
| Antiseptic, pigment and fragrance | adequate |
| Purified water | balance |

Formulation Example 10

Ointment

An ointment is prepared by a common method with the composition described in Table 6.

TABLE 6

| Ingredients | Contents (wt %) |
|---|---|
| 5-Adamantan-1-yl-N-(2,4-dihydroxybenzyl)-2,4-dimethoxybenzamide | 1.5 |
| Glycerin | 8.0 |
| Butylene glycol | 4.0 |
| Liquid paraffin | 15.0 |
| β-Glucan | 7.0 |
| Carbomer | 0.1 |
| Caprylic/capric triglyceride | 3.0 |
| Squalane | 1.0 |
| Cetearyl glucoside | 1.5 |
| Sorbitan stearate | 0.4 |
| Cetearyl alcohol | 1.0 |
| Beeswax | 4.0 |
| Antiseptic, pigment and fragrance | adequate |
| Purified water | balance |

What is claimed is:

1. A method for inhibiting one or more of the following activities in a subject suffering from inflammation:
(i) the production of one or more of NO and PGE2;
(ii) the expression of one or more of iNOS and COX-2;
(iii) the activity of one or more of the transcription factors NF-κB and AP-1;
(iv) the expression of the proinflammatory cytokine IL-1β,
wherein the method comprises administering an effective amount of 5-adamantan-1-yl-N-(2,4-dihydroxybenzyl)-2,4-dimethoxybenzamide of Chemical Formula 1, a pharmaceutically acceptable salt thereof, a hydrate thereof or a solvate thereof to a subject in need thereof:

[Chemical Formula 1]

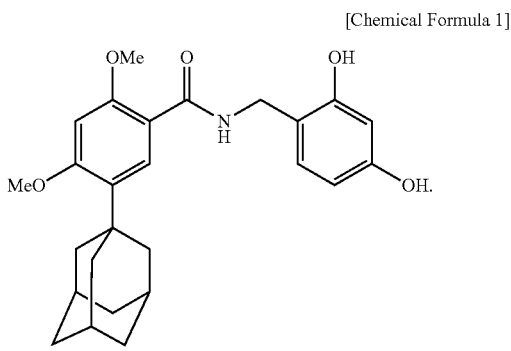 [SMILES: COc1cc(OC)c(C23CC4CC(CC(C4)C2)C3)cc1C(=O)NCc1ccc(O)cc1O]

2. The method according to claim 1, wherein the 5-adamantan-1-yl-N-(2,4-dihydroxybenzyl)-2,4-dimethoxybenzamide of Chemical Formula 1, the pharmaceutically acceptable salt thereof, the hydrate thereof or the solvate thereof inhibits the production of one or more of NO and PGE2.

3. The method according to claim 1, wherein the 5-adamantan-1-yl-N-(2,4-dihydroxybenzyl)-2,4-dimethoxybenzamide of Chemical Formula 1, the pharmaceutically acceptable salt thereof, the hydrate thereof or the solvate thereof inhibits the expression of one or more of iNOS and COX-2.

4. The method according to claim 1, wherein the 5-adamantan-1-yl-N-(2,4-dihydroxybenzyl)-2,4-dimethoxybenzamide of Chemical Formula 1, the pharmaceutically acceptable salt thereof, the hydrate thereof or the solvate thereof inhibits the activity of one or more of the transcription factors NF-κB and AP-1.

5. The method according to claim 1, wherein the 5-adamantan-1-yl-N-(2,4-dihydroxybenzyl)-2,4-dimethoxybenzamide of Chemical Formula 1, the pharmaceutically acceptable salt thereof, the hydrate thereof or the solvate thereof inhibits the expression of the proinflammatory cytokine IL-1β.

6. The method according to claim 1, wherein the 5-adamantan-1-yl-N-(2,4-dihydroxybenzyl)-2,4-dimethoxybenzamide of Chemical Formula 1, the pharmaceutically acceptable salt thereof, the hydrate thereof or the solvate thereof is administered in a form of composition, and the amount of 5-adamantan-1-yl-N-(2,4-dihydroxybenzyl)-2,4-dimethoxybenzamide of Chemical Formula 1, the pharmaceutically acceptable salt thereof, the hydrate thereof or the solvate thereof is 0.01-20 wt % based on the total weight of the composition.

7. The method according to claim 6, wherein the composition is a cosmetic composition.

8. The method according to claim 6, wherein the composition is a food composition.

9. The method according to claim 6, wherein the composition is a pharmaceutical composition.

* * * * *